(12) United States Patent
Ransden et al.

(10) Patent No.: US 8,317,690 B2
(45) Date of Patent: Nov. 27, 2012

(54) FOAM PORT AND INTRODUCER ASSEMBLY

(75) Inventors: Jeffrey E. Ransden, Fairfield, CT (US); Leland R. Adams, Ansonia, CT (US); Joel A. Helfer, Cheshire, CT (US); Alan B. Bachman, Milford, CT (US); Adam I. Lehman, Northford, CT (US)

(73) Assignee: Covidien LP, Mansfield, MA (US)

( * ) Notice: Subject to any disclaimer, the term of this patent is extended or adjusted under 35 U.S.C. 154(b) by 270 days.

(21) Appl. No.: 12/719,341

(22) Filed: Mar. 8, 2010

(65) Prior Publication Data

US 2010/0249524 A1    Sep. 30, 2010

Related U.S. Application Data

(60) Provisional application No. 61/164,977, filed on Mar. 31, 2009.

(51) Int. Cl.
*A61B 1/32* (2006.01)

(52) U.S. Cl. .......................... 600/207; 600/206

(58) Field of Classification Search .................. 600/114, 600/115, 201–246; 604/506, 539, 514; 606/108, 606/191, 197–199; 623/1.27
See application file for complete search history.

(56) References Cited

U.S. PATENT DOCUMENTS

| | | | |
|---|---|---|---|
| 4,016,884 A | 4/1977 | Kwan-Gett |
| 4,112,932 A | 9/1978 | Chiulli |
| 4,183,357 A | 1/1980 | Bentley et al. |
| 4,402,683 A | 9/1983 | Kopman |
| 4,653,476 A | 3/1987 | Bonnet |
| 4,863,430 A | 9/1989 | Klyce et al. |
| 4,863,438 A | 9/1989 | Gauderer et al. |
| 5,073,169 A | 12/1991 | Raiken |
| 5,082,005 A | 1/1992 | Kaldany |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |

(Continued)

FOREIGN PATENT DOCUMENTS

EP    0807416    11/1997
(Continued)

OTHER PUBLICATIONS

European Search Report for corresponding EP 10 25 1317 dated Oct. 25, 2010.

*Primary Examiner* — Alvin Stewart
*Assistant Examiner* — Lynnsy Schneider

(57) ABSTRACT

A surgical portal and introducer assembly includes an introducer and a portal member positionable within a longitudinal passageway of the introducer. The portal member is adapted for positioning within a tissue tract and has at least one longitudinal port for passage of a surgical object. The portal member comprises a compressible material and is adapted to transition between a first expanded condition and a second compressed condition. The assembly may include an expandable restraining member that may be disposed within the longitudinal passageway. The restraining member is adapted to expand and compress the portal member to cause the portal member to transition to the compressed condition.

15 Claims, 3 Drawing Sheets

U.S. PATENT DOCUMENTS

| | | | |
|---|---|---|---|
| 5,312,391 A | 5/1994 | Wilk | |
| 5,330,486 A | 7/1994 | Wilk | |
| 5,334,143 A | 8/1994 | Carroll | |
| 5,345,927 A | 9/1994 | Bonutti | |
| 5,366,478 A | 11/1994 | Brinkerhoff et al. | |
| 5,375,588 A | 12/1994 | Yoon | |
| 5,378,237 A * | 1/1995 | Boussignac et al. | 604/103.01 |
| 5,391,156 A | 2/1995 | Hildwein et al. | |
| 5,395,367 A | 3/1995 | Wilk | |
| 5,437,683 A | 8/1995 | Neumann et al. | |
| 5,460,170 A | 10/1995 | Hammerslag | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,522,791 A | 6/1996 | Leyva | |
| 5,524,644 A | 6/1996 | Crook | |
| 5,540,648 A | 7/1996 | Yoon | |
| 5,545,179 A | 8/1996 | Williamson, IV | |
| 5,577,993 A | 11/1996 | Zhu et al. | |
| 5,601,581 A | 2/1997 | Fogarty et al. | |
| 5,634,911 A | 6/1997 | Hermann et al. | |
| 5,634,937 A | 6/1997 | Mollenauer et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,672,168 A | 9/1997 | de la Torre et al. | |
| 5,683,378 A | 11/1997 | Christy | |
| 5,685,857 A | 11/1997 | Negus et al. | |
| 5,713,858 A | 2/1998 | Heruth et al. | |
| 5,713,869 A | 2/1998 | Morejon | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,746,764 A * | 5/1998 | Green et al. | 606/194 |
| 5,782,817 A | 7/1998 | Franzel et al. | |
| 5,785,715 A * | 7/1998 | Schatz | 606/108 |
| 5,795,290 A | 8/1998 | Bridges | |
| 5,803,921 A | 9/1998 | Bonadio | |
| 5,810,712 A | 9/1998 | Dunn | |
| 5,810,838 A * | 9/1998 | Solar | 606/108 |
| 5,813,409 A | 9/1998 | Leahy et al. | |
| 5,830,191 A | 11/1998 | Hildwein et al. | |
| 5,836,871 A | 11/1998 | Wallace et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,860,966 A * | 1/1999 | Tower | 606/1 |
| 5,865,817 A | 2/1999 | Moenning et al. | |
| 5,871,474 A | 2/1999 | Hermann et al. | |
| 5,876,413 A | 3/1999 | Fogarty et al. | |
| 5,894,843 A | 4/1999 | Benetti et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,911,452 A * | 6/1999 | Yan | 29/516 |
| 5,916,198 A | 6/1999 | Dillow | |
| 5,941,898 A | 8/1999 | Moenning et al. | |
| 5,944,735 A * | 8/1999 | Green et al. | 606/194 |
| 5,957,913 A | 9/1999 | de la Torre et al. | |
| 5,964,781 A | 10/1999 | Mollenauer et al. | |
| 5,971,992 A * | 10/1999 | Solar | 606/108 |
| 5,976,174 A | 11/1999 | Ruiz | |
| 5,997,515 A | 12/1999 | de la Torre et al. | |
| 6,009,614 A * | 1/2000 | Morales | 29/516 |
| 6,017,355 A | 1/2000 | Hessel et al. | |
| 6,018,094 A | 1/2000 | Fox | |
| 6,024,736 A | 2/2000 | de la Torre et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,059,816 A | 5/2000 | Moenning | |
| 6,068,635 A * | 5/2000 | Gianotti | 29/235 |
| 6,068,639 A | 5/2000 | Fogarty et al. | |
| 6,077,288 A | 6/2000 | Shimomura et al. | |
| 6,086,603 A | 7/2000 | Termin et al. | |
| 6,099,506 A | 8/2000 | Macoviak et al. | |
| 6,110,154 A | 8/2000 | Shimomura et al. | |
| 6,142,936 A | 11/2000 | Beane et al. | |
| 6,171,282 B1 | 1/2001 | Ragsdale | |
| 6,197,002 B1 | 3/2001 | Peterson | |
| 6,217,555 B1 | 4/2001 | Hart et al. | |
| 6,228,063 B1 | 5/2001 | Aboul-Hosn | |
| 6,238,373 B1 | 5/2001 | de la Torre et al. | |
| 6,241,768 B1 | 6/2001 | Agarwal et al. | |
| 6,254,534 B1 | 7/2001 | Butler et al. | |
| 6,264,604 B1 | 7/2001 | Kieturakis et al. | |
| 6,315,770 B1 | 11/2001 | de la Torre et al. | |
| 6,319,246 B1 | 11/2001 | de la Torre et al. | |
| 6,371,968 B1 | 4/2002 | Kogasaka et al. | |
| 6,382,211 B1 | 5/2002 | Crook | |
| 6,423,036 B1 | 7/2002 | Van Huizen | |
| 6,440,061 B1 | 8/2002 | Wenner et al. | |
| 6,440,063 B1 | 8/2002 | Beane et al. | |
| 6,443,957 B1 | 9/2002 | Addis | |
| 6,447,489 B1 | 9/2002 | Peterson | |
| 6,450,983 B1 | 9/2002 | Rambo | |
| 6,454,783 B1 | 9/2002 | Piskun | |
| 6,464,686 B1 | 10/2002 | O'Hara et al. | |
| 6,468,292 B1 | 10/2002 | Mollenauer et al. | |
| 6,488,620 B1 | 12/2002 | Segermark et al. | |
| 6,488,692 B1 | 12/2002 | Spence et al. | |
| 6,527,787 B1 | 3/2003 | Fogarty et al. | |
| 6,551,270 B1 | 4/2003 | Bimbo et al. | |
| 6,558,371 B2 | 5/2003 | Dorn | |
| 6,576,009 B2 * | 6/2003 | Ryan et al. | 623/1.35 |
| 6,578,577 B2 | 6/2003 | Boandio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,669,674 B1 | 12/2003 | Macoviak et al. | |
| 6,676,639 B1 | 1/2004 | Ternström | |
| 6,706,050 B1 | 3/2004 | Giannadakis | |
| 6,723,044 B2 | 4/2004 | Pulford et al. | |
| 6,723,088 B2 | 4/2004 | Gaskill, III et al. | |
| 6,725,080 B2 | 4/2004 | Melkent et al. | |
| 6,745,445 B2 * | 6/2004 | Spilka | 29/407.08 |
| 6,800,084 B2 | 10/2004 | Davison et al. | |
| 6,811,546 B1 | 11/2004 | Callas et al. | |
| 6,814,078 B2 | 11/2004 | Crook | |
| 6,840,946 B2 | 1/2005 | Fogarty et al. | |
| 6,840,951 B2 | 1/2005 | de la Torre et al. | |
| 6,846,287 B2 | 1/2005 | Bonadio et al. | |
| 6,863,674 B2 | 3/2005 | Kasahara et al. | |
| 6,878,110 B2 | 4/2005 | Yang et al. | |
| 6,890,295 B2 | 5/2005 | Michels et al. | |
| 6,913,609 B2 | 7/2005 | Yencho et al. | |
| 6,916,310 B2 | 7/2005 | Sommerich | |
| 6,916,331 B2 | 7/2005 | Mollenauer et al. | |
| 6,929,637 B2 | 8/2005 | Gonzalez et al. | |
| 6,939,296 B2 | 9/2005 | Ewers et al. | |
| 6,945,932 B1 | 9/2005 | Caldwell et al. | |
| 6,958,037 B2 | 10/2005 | Ewers et al. | |
| 6,972,026 B1 | 12/2005 | Caldwell et al. | |
| 6,991,602 B2 | 1/2006 | Nakazawa et al. | |
| 6,997,909 B2 | 2/2006 | Goldberg | |
| 7,001,397 B2 | 2/2006 | Davison et al. | |
| 7,008,377 B2 | 3/2006 | Beane et al. | |
| 7,014,628 B2 | 3/2006 | Bousquet | |
| 7,033,319 B2 | 4/2006 | Pulford et al. | |
| 7,052,454 B2 | 5/2006 | Taylor | |
| 7,056,321 B2 | 6/2006 | Pagliuca et al. | |
| 7,077,852 B2 | 7/2006 | Fogarty et al. | |
| 7,081,089 B2 | 7/2006 | Bonadio et al. | |
| 7,083,626 B2 | 8/2006 | Hart et al. | |
| 7,100,614 B2 | 9/2006 | Stevens et al. | |
| 7,101,353 B2 | 9/2006 | Lui et al. | |
| 7,153,261 B2 | 12/2006 | Wenchell | |
| 7,163,510 B2 | 1/2007 | Kahle et al. | |
| 7,192,436 B2 | 3/2007 | Sing et al. | |

| | | |
|---|---|---|
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,766,824 B2 | 8/2010 | Jensen et al. |
| 7,798,898 B2 | 9/2010 | Luciano, Jr. et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,896,889 B2 | 3/2011 | Mazzocchi et al. |
| 7,909,760 B2 | 3/2011 | Albrecht et al. |
| 8,020,275 B2 * | 9/2011 | Sarac et al. ................ 29/460 |
| 2001/0037053 A1 | 11/2001 | Bonadio et al. |
| 2002/0038077 A1 | 3/2002 | de la Torre et al. |
| 2002/0183594 A1 | 12/2002 | Beane et al. |
| 2003/0014076 A1 | 1/2003 | Mollenauer et al. |
| 2003/0105473 A1 | 6/2003 | Miller |
| 2003/0135091 A1 | 7/2003 | Nakazawa et al. |
| 2003/0236549 A1 | 12/2003 | Bonadio et al. |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0073090 A1 | 4/2004 | Butler et al. |
| 2004/0088038 A1 * | 5/2004 | Dehnad et al. ............. 623/1.15 |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0240082 A1 | 10/2005 | Bonadio et al. |
| 2005/0241647 A1 | 11/2005 | Nguyen et al. |
| 2005/0267419 A1 | 12/2005 | Smith |
| 2005/0288558 A1 | 12/2005 | Ewers et al. |
| 2006/0020241 A1 | 1/2006 | Piskun et al. |
| 2006/0030755 A1 | 2/2006 | Ewers et al. |
| 2006/0071432 A1 | 4/2006 | Staudner |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0229501 A1 | 10/2006 | Jensen et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0270911 A1 | 11/2006 | Voegele et al. |
| 2007/0088202 A1 | 4/2007 | Albrecht et al. |
| 2007/0088204 A1 | 4/2007 | Albrecht et al. |
| 2007/0088241 A1 | 4/2007 | Brustad et al. |
| 2007/0088258 A1 | 4/2007 | Wenchell et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0225569 A1 | 9/2007 | Ewers et al. |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097350 A1 * | 4/2008 | Bell et al. .................. 604/266 |
| 2008/0161826 A1 | 7/2008 | Guiraudon |
| 2008/0200767 A1 | 8/2008 | Ewers et al. |
| 2008/0255519 A1 | 10/2008 | Piskun et al. |
| 2008/0319261 A1 | 12/2008 | Lucini |
| 2009/0012477 A1 | 1/2009 | Norton et al. |
| 2009/0093752 A1 | 4/2009 | Richard et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0187079 A1 | 7/2009 | Albrecht et al. |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2009/0326461 A1 | 12/2009 | Gresham |
| 2010/0063452 A1 | 3/2010 | Edelman et al. |
| 2010/0100043 A1 | 4/2010 | Racenet |
| 2010/0240960 A1 | 9/2010 | Richard |
| 2010/0249516 A1 | 9/2010 | Shelton, IV et al. |
| 2010/0312061 A1 | 12/2010 | Hess et al. |

FOREIGN PATENT DOCUMENTS

| | | |
|---|---|---|
| EP | 0950376 | 10/1999 |
| EP | 1312318 | 5/2003 |
| EP | 1312318 B1 | 12/2005 |
| EP | 1 774 918 A1 | 4/2007 |
| EP | 2044889 | 4/2009 |
| EP | 2044889 A1 | 4/2009 |
| EP | 2044897 | 4/2009 |
| EP | 2098182 | 9/2009 |
| EP | 2181657 | 5/2010 |
| EP | 2 289 438 | 3/2011 |
| WO | WO 93/14801 | 8/1993 |
| WO | WO93/14801 | 8/1993 |
| WO | WO 94/04067 | 3/1994 |
| WO | WO96/36283 | 11/1996 |
| WO | WO 97/33520 | 9/1997 |
| WO | WO 97/42889 | 11/1997 |
| WO | WO97/42889 | 11/1997 |
| WO | WO 99/16368 | 4/1999 |
| WO | WO 99/22804 | 5/1999 |
| WO | WO00/32120 | 6/2000 |
| WO | WO01/08581 | 2/2001 |
| WO | WO01/32116 | 5/2001 |
| WO | WO 01/49363 A1 | 7/2001 |
| WO | WO 02/07611 A2 | 1/2002 |
| WO | WO03/034908 | 5/2003 |
| WO | WO03/071926 | 9/2003 |
| WO | WO2004/043275 | 5/2004 |
| WO | WO2004/054456 | 7/2004 |
| WO | WO2004/075741 | 9/2004 |
| WO | WO2004/075930 | 9/2004 |

| | | |
|---|---|---|
| WO | WO2006/019723 | 2/2006 |
| WO | WO2006/100658 | 9/2006 |
| WO | WO 2006/100658 A2 | 9/2006 |
| WO | WO2006/110733 | 10/2006 |
| WO | WO 2006/115893 | 11/2006 |
| WO | WO 2008/011358 | 1/2008 |
| WO | WO2008/015566 | 2/2008 |
| WO | WO 2008/015566 A2 | 2/2008 |
| WO | WO2008/042005 | 4/2008 |
| WO | WO 2008/093313 A1 | 8/2008 |
| WO | WO2008/103151 | 8/2008 |
| WO | WO2008/012194 | 10/2008 |
| WO | WO 2008/121294 A1 | 10/2008 |
| WO | WO2009/036343 | 3/2009 |

* cited by examiner

FOAM PORT AND INTRODUCER ASSEMBLY

CROSS REFERENCE TO RELATED APPLICATION

The present application claims the benefit of and priority to U.S. Provisional Application Ser. No. 61/164,977 filed on Mar. 31, 2009, the entire contents of which are incorporated herein by reference.

BACKGROUND

1. Technical Field

The present disclosure relates generally to ports for use in minimally invasive surgical procedures, such as endoscopic and/or laparoscopic procedures, and more particularly, relates to an access port and an associated introducer to assist in deploying the port within a tissue tract of a patient.

2. Description of Related Art

Minimally invasive surgery is a type of surgery performed through one or more small incisions in a patient's body, usually less than an inch in dimension. Some advantages of minimal invasive surgery is that patients have less trauma to the body, lose less blood, have smaller surgical scars, and need less pain medication.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various ports with valves and seals are used during the course of minimally invasive procedures and are widely known in the art. However, a continuing need exists for an access port and associated introducer which can position the access port with relative ease and with minor inconvenience for the surgeon.

SUMMARY

Accordingly, a surgical port and introducer assembly includes an introducer having a longitudinal passageway and a portal member positionable within the longitudinal passageway of the introducer. The portal member is adapted for positioning within a tissue tract and has at least one longitudinal port for passage of a surgical object. The portal member comprises a compressible material and is adapted to transition between a first expanded condition to facilitate securing of the portal member within the tissue tract and in substantial sealed relation with tissue surfaces defining the tissue tract, and a second compressed condition to facilitate at least partial insertion of the portal member within the tissue tract. The assembly further includes an expandable restraining member at least partially disposed within the longitudinal passageway of the introducer. The restraining member is adapted to expand and compress the portal member to cause the portal member to assume the compressed condition thereof, to thereby facilitate passage of the portal member through the longitudinal passageway of the introducer and into the tissue tract.

The restraining member may be a substantially annular member defining a substantially annular opening for at least partially accommodating the portal member. The restraining member may be a balloon member adapted to expand upon the introduction of fluids. The balloon member may define a general toroidal shape.

The introducer may include an introducer housing and an elongated introducer segment extending from the introducer housing with the restraining member being disposed within the introducer housing. The introducer may further include a deployment member adapted to longitudinally advance within the longitudinal passageway of the introducer to deploy the portal member from the introducer and within the tissue tract.

The portal member may define leading and trailing ends. The at least one longitudinal port of the portal member may extend between the leading and trailing ends, and be adapted for reception of an object whereby compressible material defining the at least one port is adapted to deform to establish a substantial sealed relation with the object. The portal member may comprise one of a foam material or a gel material. The portal member may include a plurality of longitudinal ports.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1B:
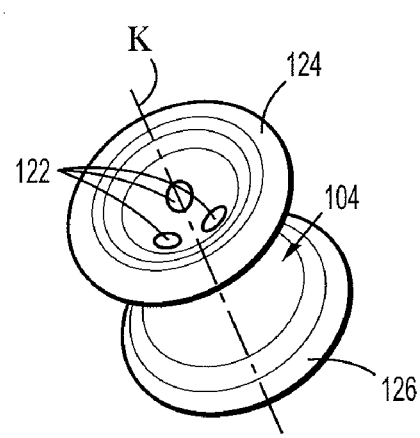
FIG. 1B is a view of a perspective view of a port of the assembly of FIG. 1A.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is further from the user. In the following description, well-known functions or constructions are not described in detail to avoid obscuring the present disclosure in unnecessary detail.

One type of minimal invasive surgery described herein is referred to as a single-incision laparoscopic surgery (SILS). SILS is an advanced minimally invasive surgical procedure which would permit a surgeon to operate through a single entry point, typically the patient's navel. The disclosed SILS procedure involves insufflating the body cavity and positioning a portal member within, e.g., the navel of the patient. Instruments including an endoscope and additional instruments such as graspers, staplers, forceps or the like may be introduced within the portal member to carry out the surgical procedure.

The port assembly in the SILS procedure may be introduced into an incision with a Kelly clamp. However, the Kelly clamp may limit the surgeon's ability to properly place a SILS port due to the limited length of the Kelly clamp's arm and handle. Furthermore, visibility may become an issue due to the presence of the clamp and the surgeon's hand holding the clamp. Removal of the Kelly clamp subsequent to placement of the port may also present undesired obstacles.

Referring now to the drawings, in which like reference numerals identify identical or substantially similar parts throughout the several views, FIGS. 1A-2B illustrates a port and introducer assembly 100 for use in, e.g., the above-identified SILS procedure. The surgical port and introducer assembly 100 includes introducer 102 and portal member 104 which is positionable within the introducer 102. Introducer 102 includes introducer housing 106 and elongate member 108 extending from the introducer housing 106. Introducer housing 106 includes an expandable member 110 mounted therein. Expandable member 110 may be any element which may expand upon reception of fluids within its interior 110a. In one embodiment, expandable member 110 is an inflatable balloon element secured within the internal volume of introducer housing 106, and adapted to expand from an initial uninflated or unexpanded state to an inflated or expanded state upon reception of fluids from fluid source 112. In one embodiment, expandable element 110 is substantially toroidal in configuration to circumscribe portal member 104 and compress the portal member 104 prior to advancement through elongate element 106. Fluid connection between fluid source 112 and expandable member 110 may be affected through any conventional means including tubing 115 as shown. Any means for securing expandable member 110 within introducer housing 110 are envisioned including cements, adhesives, spot welding or the like. Expandable element 110 may also include one or more ribs 114 disposed on the inner surface diameter of the expandable member. Ribs 114 may enhance the structural integrity of expandable member 110. In addition the ribs or struts 114 may be, for example, but not limited to, a series of poly(tetrafluoroethylene) (PTFE) lined ribs or struts 114 to aid in an effortless deployment of the compressible portal member 104 by permitting the compressible portal member 104 to slide along the ribs 114 during advancement or deployment of the compressible portal member 104 through introducer 102. Ribs 114 may include a lubricious coating such as silicon to enhance sliding movement of portal member.

Introducer housing 106 and elongate introducer segment or element 108 define longitudinal passageway 116 with respect to longitudinal axis "k" extending the length of introducer 102. Elongate element 108 is dimensioned for insertion within the tissue tract "p" and may be a sleeve element defining an internal dimension or diameter "d1". The dimension "d1" may be substantially constant along the length of elongate member 108. In the alternative, dimension "d1" may generally decrease from proximal or trailing end 118 of the elongate member 108 to distal or leading end 120. The dimension "d1" may range from about 3 mm to about 15 mm.

Portal member 104 includes at least one longitudinal port 122, possibly, a plurality of longitudinal ports 122 extending along the axis "k" of the portal member 104. At least one or more inner longitudinal ports 122 are dimensioned to receive a surgical object (not shown) therethrough. Upon introduction through a respective port 122, the inner surface portions defining the port 122 establish and maintain a substantial sealed relation about the instrument or surgical object. Portal member 104 may define an hour glass shape as shown. Trailing and leading ends 124,126 may define flange segments which may be integrally formed with portal member 104. Portal member 104 may be made from a disposable, compressible, and/or flexible type material, for example, but not limited to, a suitable foam or gel material having sufficient compliance to form a seal about one or more surgical objects, shown generally as surgical object, and also establish a sealing relation with the tissue. The foam is preferably sufficiently compliant to accommodate off axis motion of the surgical object. In one embodiment, the foam includes a polyisoprene material. Suitable portal members are disclosed in commonly assigned U.S. patent application Ser. No. 12/244,024, filed Oct. 2, 2008, the entire contents of which is hereby incorporated by reference herein.

Figure 1A:
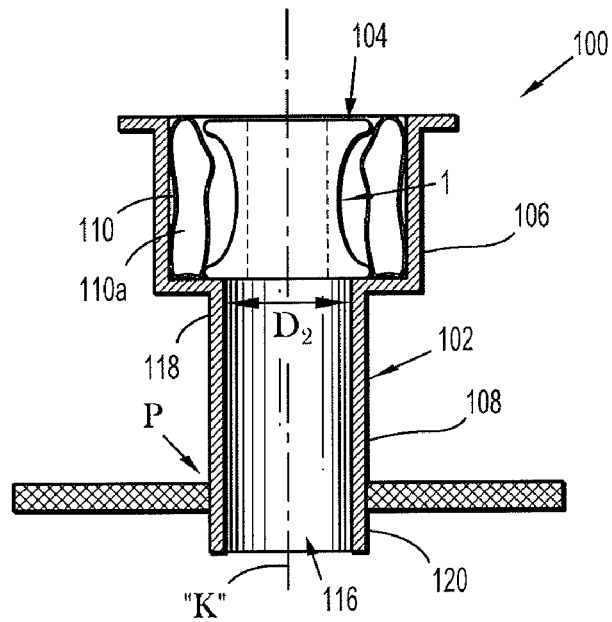
FIG. 1A is a longitudinal cross-sectional view of a surgical port and introducer assembly in accordance with the principles of the present disclosure.
Figure 2A:
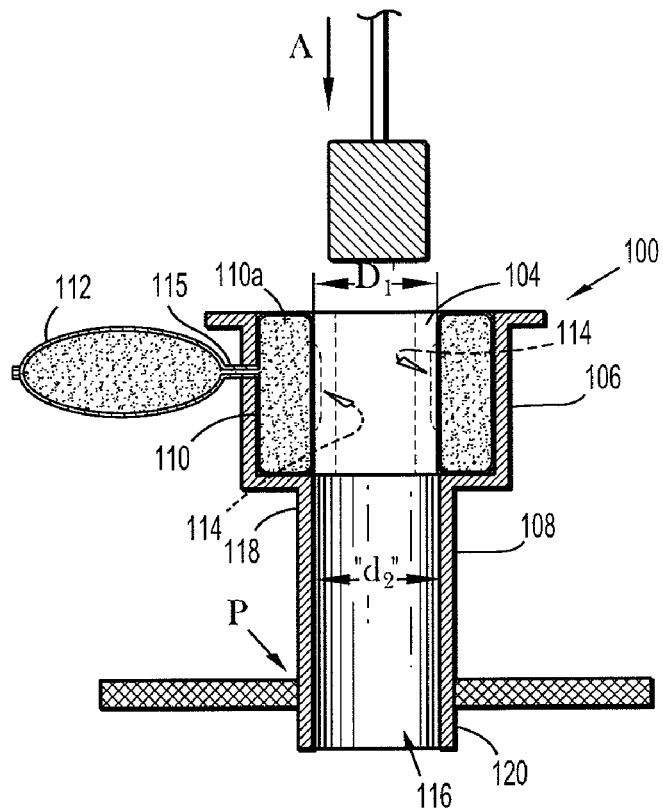
FIG. 2A is a longitudinal cross-sectional view of the surgical port and introducer assembly of FIG. 1A illustrating the expandable restraining member in an inflated state.
Figure 2B:
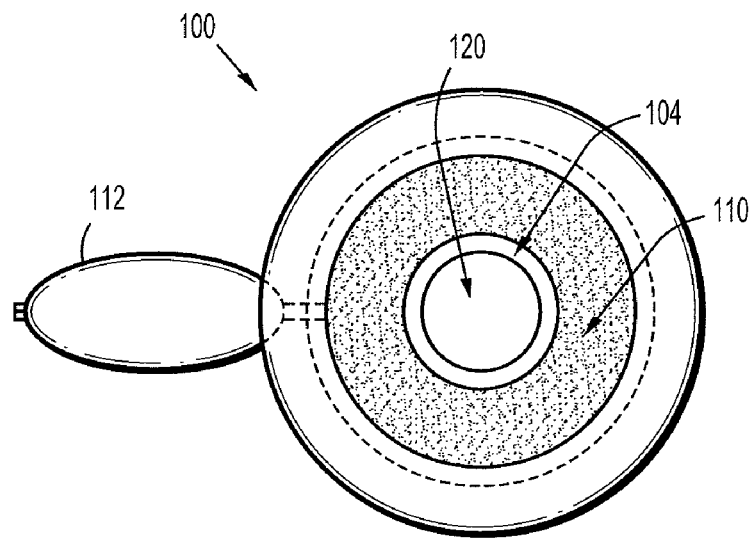
FIG. 2B is a top plan view of the surgical port and introducer assembly of FIG. 1A illustrating the expandable restraining member in an inflated state.

In use, elongate member 108 of introducer 102 is positioned within tissue tract "p" as depicted in FIG. 1A with expandable member 110 is in its unexpanded state. Portal member 104 is positioned within introducer housing 106, e.g., within the opening defined within expandable member 110. In one embodiment, introducer housing 106 and uninflated expandable member 110 are dimensioned to receive portal member 104 without compressing the portal member 104. With portal member 104 within introducer housing 106, fluid source 112 is activated to deliver fluids within expandable member 110 to inflate or expand the member 110. During expansion, expandable member 110 exerts a radial inward compressive force on portal member 104, e.g., uniformally about the periphery of the portal member 104, to reduce the outer dimension of the portal member 104 to at least the inner diameter "d1" of elongate member 104, and, even less than the internal diameter "d1" as depicted in FIG. 2A. In other words, the portal member 104 is compressed by expandable member 110 to a dimension to pass through longitudinal passageway 116 of elongate member 108, and subsequently into a tissue passage "p" of a patient's tissue.

Figure 3:
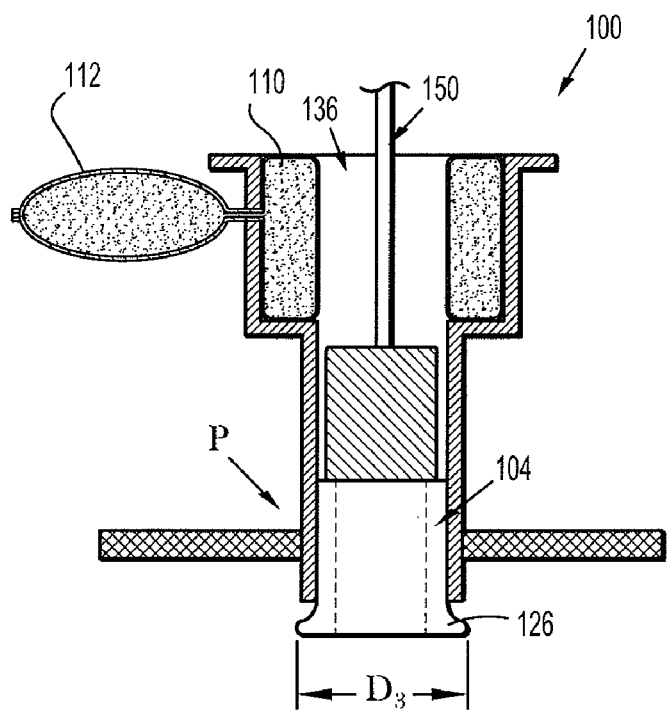
FIG. 3 is a longitudinal cross-sectional view of the surgical port and introducer assembly of FIG. 1A illustrating the compressible port being deployed into a tissue passage of a surgical site by a plunger.
Figure 4:
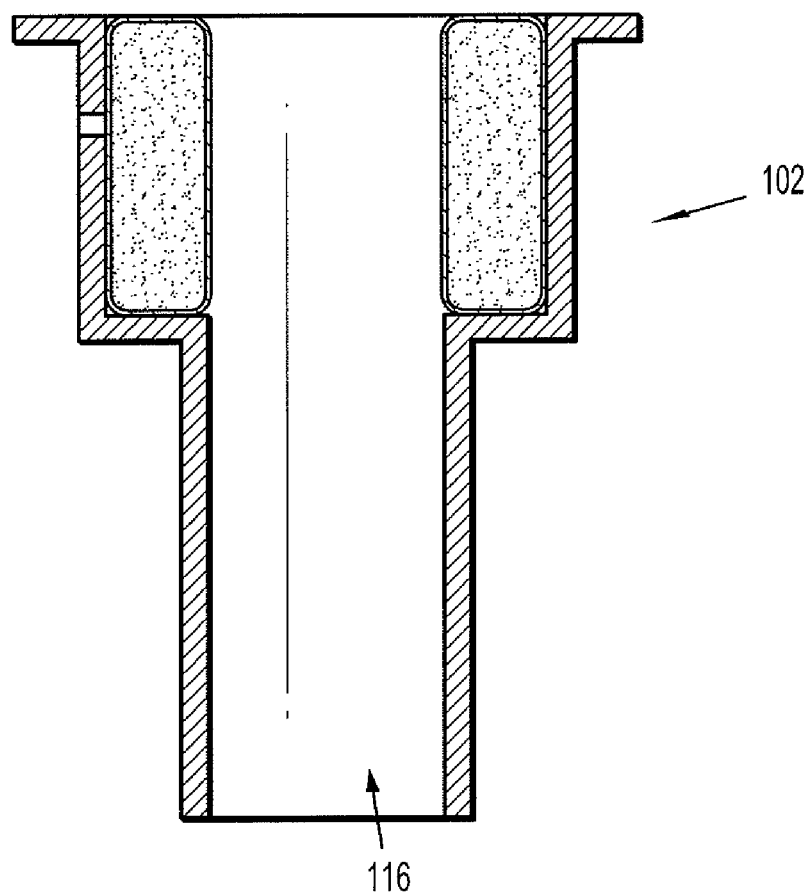
FIG. 4 is a longitudinal cross-sectional view of the surgical port and introducer assembly of FIG. 1A illustrating the port introducer removed from the surgical site and the compressible port deployed in a tissue passage of a surgical site.
Figure 4:
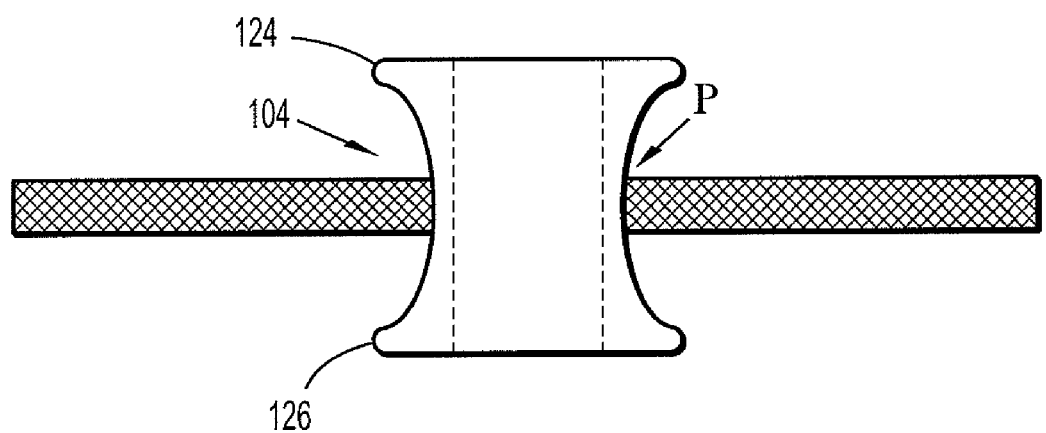

With continued reference to FIG. 2A, a plunger 128 as part of the surgical port and introducer assembly 100 is advanced within longitudinal passageway 116 of introducer 102. Plunger 128 may include plunger head 130 and plunger rod 132. Plunger 128 is advanced whereby plunger head 130 engages compressed portal member 104 and advances the portal member 104 through elongate member 108 to deploy the compressible portal member 104 into the tissue passage "p" of a patient's tissue (FIG. 3). After deployment of the portal member 104 into the tissue passage "p" of a patient, as shown in FIG. 4, the introducer 102 is removed from the tissue tract, thus allowing portal member 104 to return toward an uncompressed state. More specifically, trailing and proximal ends 124, 126 return toward their initial dimension to respectively engage opposed sides of the tissue passage "p". In addition, portal member 104 prevents the escape of fluids (e.g., gases in a laparoscopic procedure or saline in an arthroscopic procedure) by engaging the internal surfaces of the tissue passage "p" in sealed relation therewith. Thereafter, surgical instruments may be introduced within one or more longitudinal ports 122 (also in sealed relation as discussed hereinabove) to perform the desired surgery.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical portal and introducer assembly, which comprises:
an introducer defining a longitudinal axis and having a longitudinal passageway, the introducer insertable through an opening in tissue, wherein the introducer has a first end and a second end, the first end having a first outer diameter and the second end having a second outer diameter that is less than the first outer diameter;
a portal member positionable within the longitudinal passageway of the introducer, the portal member adapted for positioning within a tissue tract and having at least one longitudinal port for passage of a surgical object, the portal member comprising a compressible material and being adapted to transition between a first expanded condition to facilitate securing of the portal member within the tissue tract and in substantial sealed relation with tissue surfaces defining the tissue tract and a second compressed condition to facilitate at least partial insertion of the portal member within the tissue tract; and
an expandable restraining member at least partially disposed within the longitudinal passageway of the introducer, the restraining member adapted to expand and compress the portal member to cause the portal member to assume the compressed condition thereof, to thereby facilitate passage of the portal member through the longitudinal passageway of the introducer and into the tissue tract.

2. The surgical assembly according to claim 1 wherein the restraining member is a substantially annular member defining a substantially annular opening for at least partially accommodating the portal.

3. The surgical assembly according to claim 2 wherein the restraining member is a balloon member adapted to expand upon the introduction of fluids.

4. The surgical assembly according to claim 3 wherein the balloon member defines a general toroidal shape.

5. The surgical assembly according to claim 2 wherein the introducer includes an introducer housing and an elongated introducer segment extending from the introducer housing.

6. The surgical assembly according to claim 5 wherein the restraining member is disposed within the introducer housing.

7. The surgical assembly according to claim 6 wherein the introducer further includes a deployment member adapted to longitudinally advance within the longitudinal passageway of the introducer to deploy the portal member from the introducer and within the tissue tract.

8. The surgical assembly according to claim 7 wherein the restraining member is a balloon member adapted to expand upon the introduction of fluids.

9. The surgical assembly according to claim 8 wherein the balloon member includes a plurality of internal ribs extending in a general longitudinal direction, the ribs facilitating sliding movement of the portal member within the longitudinal passageway of the introducer during advancement of the deployment member.

10. The surgical assembly according to claim 1 wherein the portal member defines leading and trailing ends, the at least one longitudinal port extending between the leading and trailing ends and being adapted for reception of an object whereby compressible material defining the at least one port is adapted to deform to establish a substantial sealed relation with the object.

11. The surgical assembly according to claim 1 wherein the portal member comprises one of a foam material or a gel material.

12. The surgical assembly according to claim 1 wherein the portal member includes a plurality of longitudinal ports.

13. A surgical portal and introducer assembly comprising:
an introducer having a longitudinal passageway and insertable through an opening in tissue, wherein the longitudinal passageway has a proximal region and a distal region, the proximal region having a first diameter and the distal region having a second diameter that is less than the first diameter;
a portal positionable within the longitudinal passageway of the introducer, the portal having at least one longitudinal port for receiving a surgical object therethrough, the portal formed of a compressible material, and transitionable between an expanded condition and a compressed condition, the portal translatable through at least a portion of the longitudinal passageway when it is in the compressed condition, wherein the expanded condition of the portal is less than the diameter of the proximal region and greater than the diameter of the distal region; and
an expandable restraining member at least partially disposed within the longitudinal passageway, the restraining member expandable to compress the portal thereby transitioning the portal to the compressed condition such that the portal is translatable through the longitudinal passageway.

14. The surgical portal and introducer assembly of claim 13, wherein the compressed condition of the portal is less than the diameter of the proximal region and substantially similar to the diameter of the distal region.

15. The surgical portal and introducer assembly of claim 13, further including a deployment member positionable in the longitudinal passageway for translating the portal through the longitudinal passageway.

* * * * *